United States Patent
Blazey et al.

(10) Patent No.: US 6,394,963 B1
(45) Date of Patent: May 28, 2002

(54) TECHNIQUE FOR DIAGNOSING ATTENTION DEFICIT DISORDER

(75) Inventors: Richard N. Blazey, Penfield, NY (US); Peter A. Parks, Topeka, KS (US); David L. Patton, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/597,610

(22) Filed: Jun. 20, 2000

(51) Int. Cl.$^7$ ............................................. A61B 5/00
(52) U.S. Cl. ................................. 600/549; 600/300
(58) Field of Search ...................... 600/27, 549, 300, 600/301; 128/898

(56) References Cited

U.S. PATENT DOCUMENTS

| | | | | |
|---|---|---|---|---|
| 4,902,274 A | * | 2/1990 | Gleeson, III | 600/27 |
| 5,036,858 A | * | 8/1991 | Carter et al. | 600/545 |
| 5,219,322 A | * | 6/1993 | Weathers | 600/27 |
| 5,377,100 A | | 12/1994 | Pope et al. | 600/545 |
| 5,913,310 A | | 6/1999 | Brown | 128/897 |
| 5,947,908 A | * | 9/1999 | Morris | 600/484 |
| 5,995,857 A | * | 11/1999 | Toomim et al. | 600/322 |

OTHER PUBLICATIONS

Nature Magazine, Apr. 2000, vol. 6, No. 4, pp 470–473, Functional deficits in basal ganglia of children with attention–deficit/hyperactivity disorder shown with functional magnetic resonance imaging relaxometry, by Martin H. Treicher, Carl M. Anderson, Ann Polcari, Carol A. Glod, Luis C. Maas and Perry F. Renshaw.

Biofeedback and Self–Regulation, vol. 16, No. 3, 1991, Research Recognition Award paper, Disclosure on the Development of EEG Diagnostics and Biofeedbak for Attention–Deficit/Hyperactivity Disorders, by Joel F. Lubar, University of Tennessee.

Biofeedback and Self–Regulation, vol. 20, No. 4, 1995, Spectral Characteristics of Skin Temperature Indicate Peripheral Stress–Response, by Vladimir Shusterman and Ofer Barnea, Tel Aviv University.

\* cited by examiner

*Primary Examiner*—Kevin Shaver
*Assistant Examiner*—Charles Marmor, II
(74) *Attorney, Agent, or Firm*—William F. Noval

(57) ABSTRACT

A method of determining whether an individual has Attention Deficit Disorder (ADD) comprising:

sampling the peripheral skin temperature of a human subject during a predetermined time interval when the subject is in an inactive state to provide sampled peripheral skin temperature data; and analyzing the sampled peripheral skin temperature data for a pre-selected parameter, to determine whether said pre-selected parameter has a value indicative of ADD.

14 Claims, 4 Drawing Sheets

TECHNIQUE FOR DIAGNOSING ATTENTION DEFICIT DISORDER

FIELD OF THE INVENTION

This invention relates in general to a technique for diagnosing Attention Deficit Disorder (ADD) and more particularly to a technique for measuring an individual's peripheral temperature to determine values indicative of ADD.

BACKGROUND OF THE INVENTION

ADD (with and without hyperactivity) is the most common neurobehavioral disorder of childhood as well as among the most prevalent health conditions affecting school-aged children. Between 4% and 12% of school age children (several millions) are affected. $3 billion is spent annually on behalf of students with ADD. Moreover, in the general population, 9.2% of males and 2.9% of females are found to have behavior consistent with ADD. Upwards of 10 million adults may be affected.

ADD is a difficult disorder to diagnose. The core symptoms of ADD in children include inattention, hyperactivity, and impulsivity. ADD children may experience significant functional problems, such as school difficulties, academic underachievement, poor relationships with family and peers, and low self-esteem. Adults with ADD often have a history of losing jobs, impulsive actions, substance abuse, and broken marriages. ADD often goes undiagnosed if not caught at an early age and affects many adults who may not be aware of the condition. ADD has many look-alike causes (family situations, motivations) and co-morbid conditions (depression, anxiety, learning disabilities).

Diagnosis of ADD involves a process of elimination using written and verbal tests. However, there is no one objective, independent valid test for ADD. Various objective techniques have been proposed but have not yet attained acceptance. These include:

1. The eye problem called convergence insufficiency was found to be three times more common in children with ADD than in other children by University of California, San Diego researchers.
2. Infrared tracking to measure difficult-to-detect movements of children during attention tests combined with functional MRI imaging of the brain were used by psychiatrists at McLean Hospital in Belmont, Massachusetts to diagnose ADD in a small group of children (*Nature Medicine*, Vol. 6, No. 4, April 2000, Pages 470–473).
3. Techniques based on EEG biofeedback for the diagnoses and treatment of ADD are described by Lubar (*Biofeedback and Self-Regulation*, Vol. 16, No. 3, 1991, Pages 201–225).
4. U.S. Pat. No. 5,913,310, issued Jun. 22, 1999, inventor Brown, discloses a video game for the diagnosis and treatment of ADD.
5. U.S. Pat. No. 5,377,100, issued Dec. 27, 1994, inventors Pope et al., discloses a method of using a video game coupled with brain wave detection to treat patients with ADD.
6. Dr. Albert Rizzo of the Integrated Media Systems Center of the University of Southern California has used Virtual Reality techniques for the detection and treatment of ADD.

Although skin temperature spectral characteristics have been shown to indicate stress-related changes of peripheral vasomotor activity in normal subjects, there has been no disclosure of use of variations in skin-temperature response to assist in diagnosing ADD. (See: Biofeedback and Self-Regulation, Vol. 20, No. 4, 1995).

There is thus a need for a simple, inexpensive, and reliable technique for assisting in the diagnosis of ADD.

SUMMARY OF THE INVENTION

According to the present invention, there is provided a solution to the problems and fulfillment of the needs discussed above.

According to a feature of the present invention, there is provided a method of determining whether an individual has Attention Deficit Disorder (ADD) comprising:

sampling the peripheral skin temperature of a human subject during a predetermined time interval when the subject is in an inactive state to provide sampled peripheral skin temperature data and analyzing the sampled peripheral skin temperature data for a pre-selected parameter, to determine whether said pre-selected parameter has a value indicative of ADD.

ADVANTAGEOUS EFFECT OF THE INVENTION

The invention has the following advantages.

1. A technique for diagnosing ADD is provided which is simple, inexpensive and reliable.

DETAILED DESCRIPTION OF THE INVENTION

According to the invention, it has been found that a signature of ADD is hidden in fluctuation of the temperature of the skin as measured at the extremities such as at a fingertip. Biofeedback practitioners have long used measurement of hand temperature to help subjects manage their physiology by controlling blood flow to the extremities. The literature reports that reduced blood flow to the brain is frequently found in patients with ADD.

Figure 1:
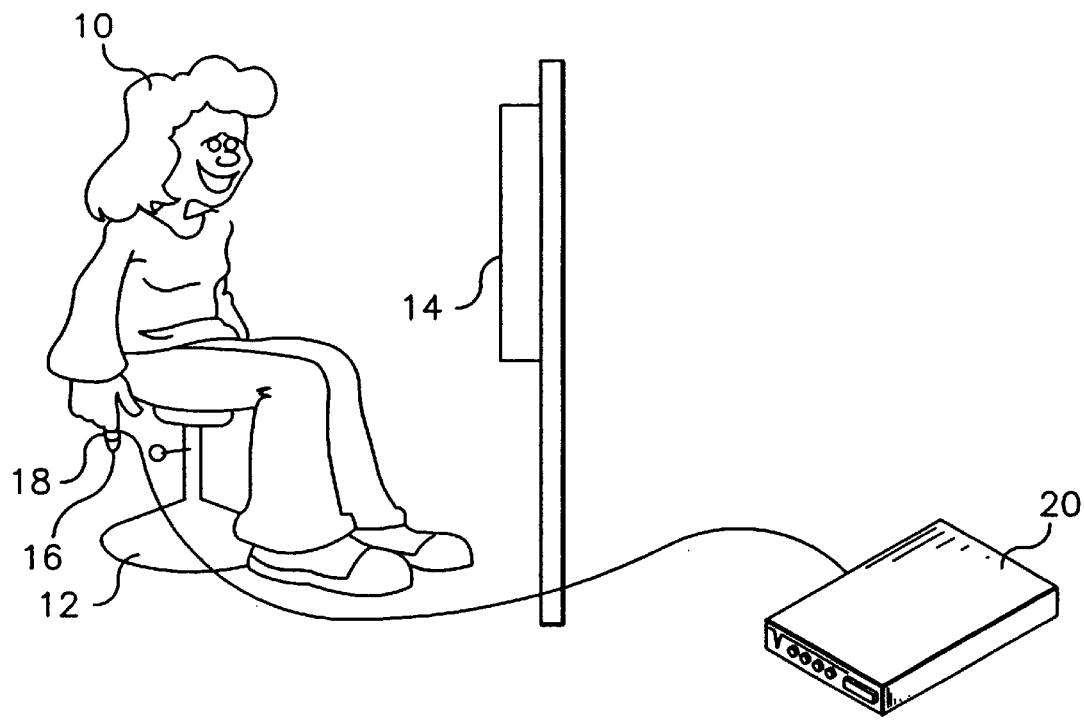
FIG. 1 is a diagrammatic view illustrating an embodiment of the present invention.

As shown in FIG. 1, a subject 10 is sitting on a chair 12 watching a screen 14. The subject is at rest in an inactive state. The temperature of a fingertip 16 of subject 10 is measured by a sensor 18. The temperature readings are supplied to module 20.

Figure 2:
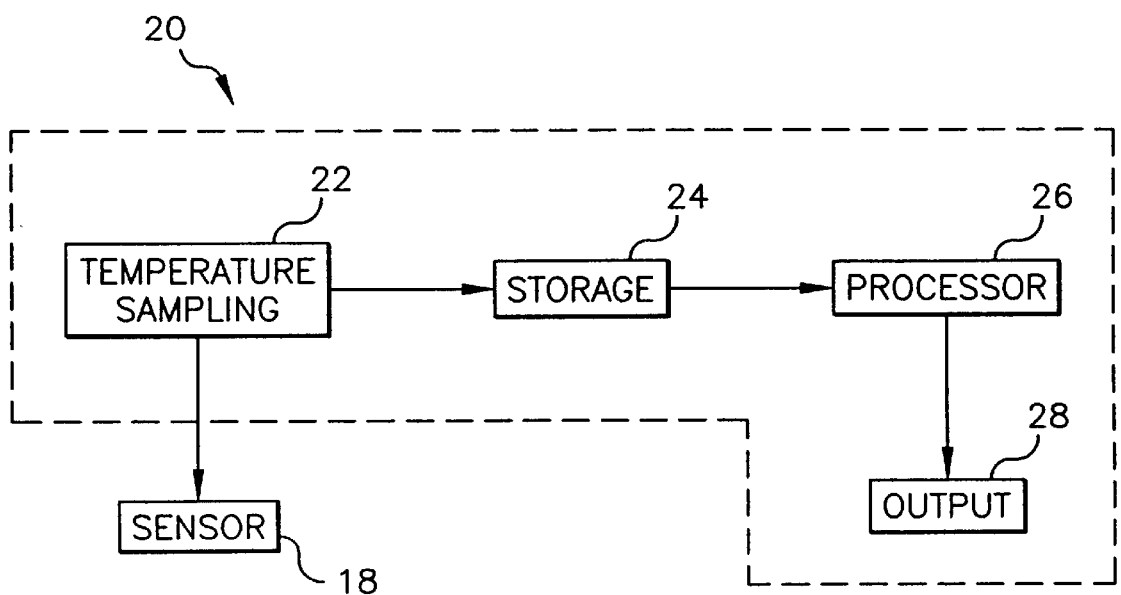
FIG. 2 is a block diagram of a system incorporating the present invention.

As shown in FIG. 2, module 20 includes temperature sampling circuit 22, data storage 24, data processor 26 and output 28 such as a display.

In FIG. 1, the fingertip temperature is first recorded during an interval when the subject 10 has been asked to sit quietly for a period of about 10 minutes. The temperature data is sampled by 22 at a time interval $\Delta t$ creating a list of N temperature samples which are stored in storage 24. The N samples are divided into groups of m samples each group corresponding to a given time window of width $\delta t$ (~32–64 sec) equally spaced in time (~50 sec) across the entire data collection time interval $\Delta t$. The data from each window is then passed through a Fast Fourier Transform (FFT) algorithm in processor 26 producing $2_{m-1}$ data points spaced equally in frequency space. The values are complex numbers having form $$FFT(f_n)=A(f_n)+B(f_n)i$$

where i is the $\sqrt{-1}$. The Phase $\Phi(f_n)$ is then found from the equation $$\Phi(f_n) = \text{Tan}^{-1}\left(\frac{B(f_n)}{A(f_n)}\right) \quad (.00)$$

and the Magnitude $M(f_n)$ from $$M(f_n) = \sqrt{B(f_n)^2 + A(f_n)^2} \quad (0.0)$$

Figure 3:
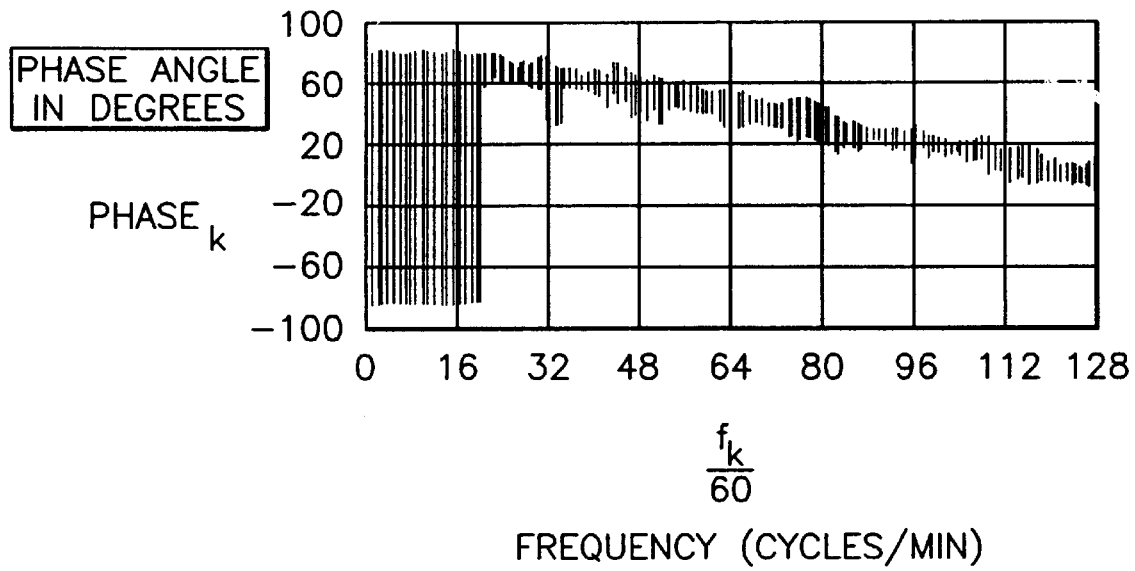
FIGS. 3–5 are graphical views useful in explaining the present invention.
Figure 4:
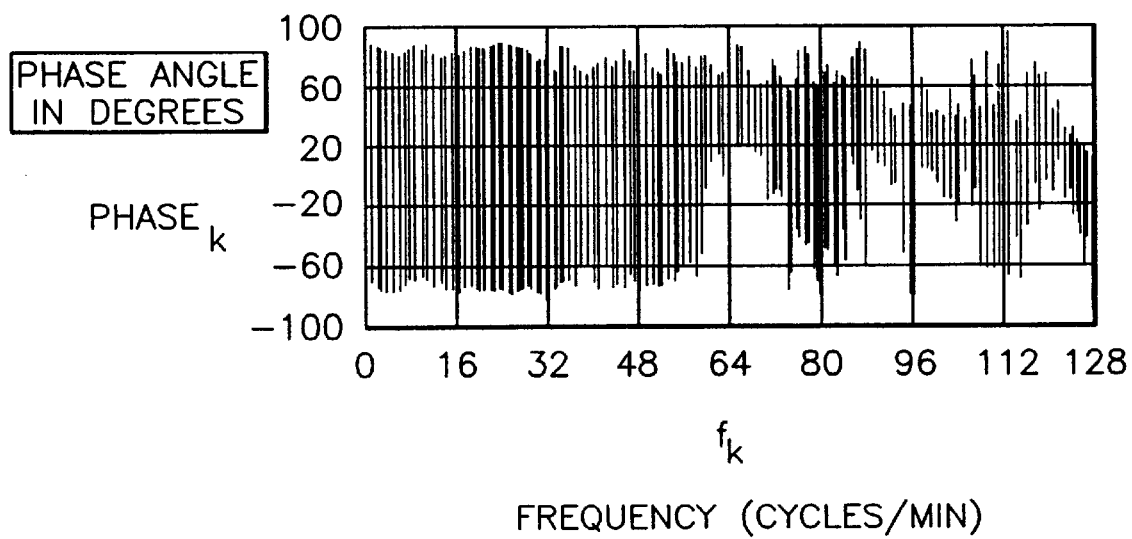
Figure 7:
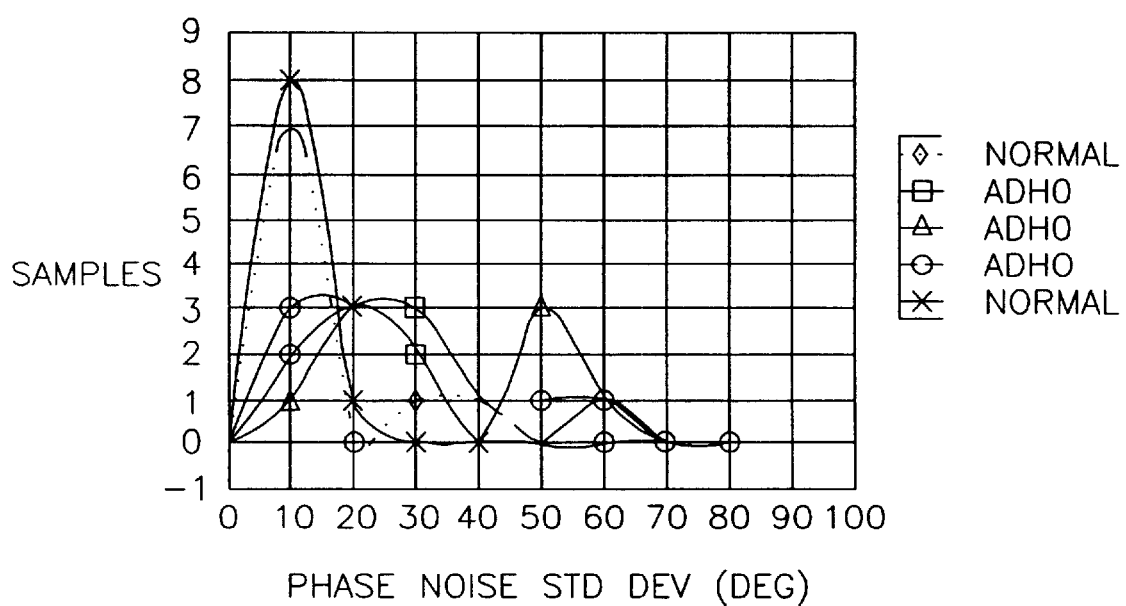
FIG. 7 is a histogram of phase noise.

FIGS. 3 and 4 respectively graphically illustrate the phase transform for a normal subject and a person diagnosed with ADD and a normal subject. The magnitude spectrum undergoes dramatic changes essentially changing from a hyperbolic curve to a flat response and simultaneously the phase exhibits a burst of noise we call phase noise. FIG. 7 shows histograms of the phase noise data taken from subjects with diagnosed ADD and normal subjects. We measure the phase noise during a time window $\Delta t$. The data in FIG. 7 is a histogram of the standard deviation $\sigma$ of the phase noise during 10 of these windows spaced equally across the 10 minute duration of the experimental period. Subjects with a diagnosis of ADD generally show significantly more phase noise than the normal subjects as evidenced by the fact that there are many more samples at high values of the $\sigma$ we use as a phase noise metric than for the normal subjects.

The following is another feature of the present invention:

Raw Data

The raw data $T_{i,k}(t)$ is the temperature taken at a fingertip during the 10-minute baseline period, which preceded each session of the VIBE project. The sessions were taken over a period of weeks or months. Some subjects had as few as 2 sessions and some as many as 5 sessions k is used to represent the session.

Windows

The data for each session were divided into a series of windows prior to performing the Fourier Transform operation. Call the window width w. In the data reported in FIG. 5, the window width was 64 seconds and there were 10 windows spaced at 50 second intervals (the windows overlap) across the 600 sec baseline spanning the range of 100–500 sec. The window number in a session is referred to with the letter j. For each window a FFT algorithm calculates the Fourier Transform F(f). The Magnitude and Phase of this transform are defined as given above. The range of magnitude variation during a window is given below where $f_{max}$ and $f_{min}$ are the frequencies where the Magnitude is the greatest and the least respectively (note the dc component at frequency zero is excluded).

Session Mean and Standard Deviation

The mean magnitude range for subject i during session k is found from equation 1.0. where m is the number of windows in the session.

$$\langle M_{i,k} \rangle = \frac{\sum_{j=1}^{m} [M(f_{max})_j - M(f_{min})_j]}{m} \quad (1.0)$$

And the corresponding standard deviation is:

$$\langle s_{i,k} \rangle = \sqrt{\frac{\sum_{j=1}^{m} \{[M(f_{max})_j - M(f_{min})_j] - \langle M_{i,k} \rangle\}^2}{m-1}} \quad (1.1)$$

Combining these session means and standard deviations over all the sessions n that a subject attended gives the ensemble mean $\mu_i$ and ensemble standard deviation. $\sigma_i$ $$\mu_i = \frac{\sum_{k=1}^{n} \langle M_{i,k} \rangle}{n} \quad (1.2)$$

and correspondingly the ensemble standard deviation is $$\langle \sigma_i \rangle = \frac{\sum_{k=1}^{n} s_{i,k}}{n} \quad (1.3)$$

Chart

Figure 5:
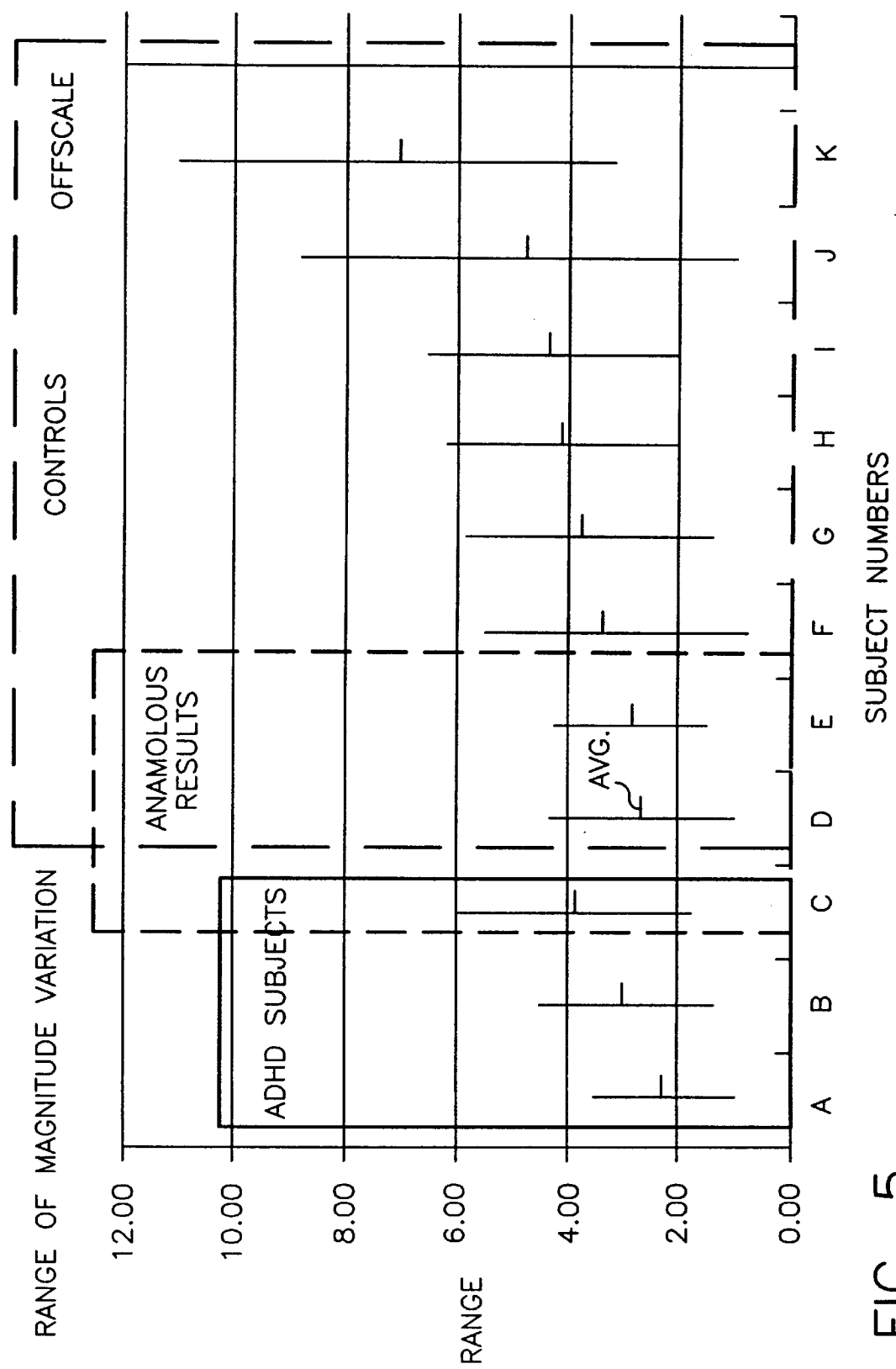

FIG. 5 is a chart comparing all the subject data in a data base. For each subject the curve shows the ensemble mean $\mu_i$ given from equation 1.2 and the I standard deviation limits defined by equations 1.4 and 1.5.

Diagnosis

Diagnosis is made from the chart by setting a threshold level for one of the parameters. Below that limit, the subject is diagnosed with ADD above the limit, the subject is called normal. In the chart the limit is set at a value of $\mu_i$ of 3.0. which yields one false negative (subject with >3.0 who says he has ADD) and two false positives (subjects who are less than 3.0 and do not report a diagnosis of ADD).

Figure 6:
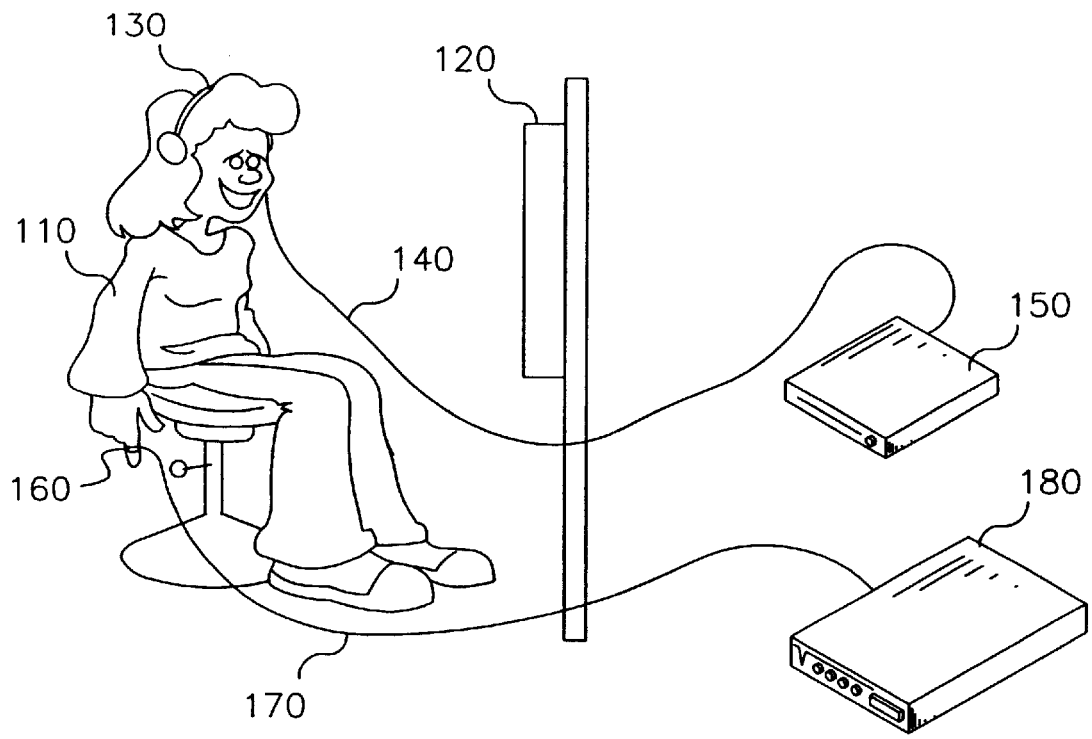
FIG. 6 is a diagrammatic view of another embodiment of the present invention.

FIG. 6 illustrates a schematic view of a subject and apparatus of another embodiment of the present invention. Shown is a subject 110, viewing a screen 120, wearing a set of earphones 130 connected via a wire 140 to a sound generating device 150. The subject's 110 skin temperature is monitored via a finger temperature sensor 160 connected via a wire 170 to a control and recording device 180. The earphone 130 maybe used to block out ambient noise or to produce a white noise intended to reduce or eliminate the audio stimulus from the environment during the test.

The invention has been described in detail with particular reference to certain preferred embodiments thereof, but it will be understood that variations and modifications can be effected within the spirit and scope of the invention.

PARTS LIST

| | |
|---|---|
| 10 | human subject |
| 12 | chair |
| 14 | screen |
| 16 | fingertip |
| 18 | sensor |
| 20 | module |
| 22 | temperature sampling circuit |
| 24 | data storage |
| 26 | data processor |
| 28 | output |
| 110 | human subject |
| 120 | viewing screen |
| 130 | earphones |
| 140 | wire |
| 150 | sound generating device |
| 160 | finger temperature sensor |
| 170 | wire |
| 180 | recording device |

What is claimed is:

1. A method of determining whether an individual has Attention Deficit Disorder (ADD) comprising:
sampling the peripheral skin temperature of a human subject during a predetermined time interval when the subject is in an inactive state to provide sampled peripheral skin temperature data; and
analyzing the sampled peripheral skin temperature data for a pre-selected parameter, to determine whether said pre-selected parameter has a value indicative of ADD.

2. The method of claim 1 wherein the skin temperature of at least one extremity of a human subject is sampled.

3. The method of claim 1 wherein the skin temperature of at least one finger of a human subject is sampled.

4. The method of claim 1 wherein during said predetermined time interval when said subject is in an inactive state, the subject wears an earphone to block out ambient noise or to receive white noise to reduce or eliminate audio stimulus from the ambient environment during said time interval.

5. The method of claim 1 wherein said data is processed with a fast fourier transform algorithm to produce frequency and phase data and said phase data is used to determine whether the subject has ADD.

6. The method of claim 5 wherein said frequency and phase data is further processed to produce magnitude range data which is used to determine whether the subject has ADD.

7. The method of claim 1 wherein in said sampling the peripheral skin temperature of a human subject, N temperature samples are taken during a time interval $\Delta t$ and the N samples are divided into groups of m samples corresponding to a window of widths Sigmast equally spaced in time across $\Delta t$, and wherein in said analyzing the sampled peripheral skin temperature data, the m data from each window is processed with a fast fourier transform (FFT) producing $2^{m-1}$ data points spaced equally in frequency space.

8. The method of claim 7 wherein in said analyzing the sampled peripheral skin temperature data the following parameters are found, the phase and magnitude are found for each window, the range of magnitude variation is found for each window, and the mean magnitude range and standard deviation for all of the windows in a session and from one or more of said parameters, a pre-selected parameter indicative of ADD is determined.

9. A system for determining whether an individual has ADD comprising:
a device for sampling the peripheral skin temperature of a human subject during a predetermined time interval when the subject is in an inactive state to provide sampled peripheral skin temperature data; and
an analyzer for analyzing the sampled peripheral skin temperature data for a pre-selected parameter to determine whether said pre-selected parameter has a value indicative of ADD.

10. The system of claim 9 wherein said device includes a sensor for sensing the skin temperature of at least one extremity of a human subject.

11. The system of claim 9 wherein said device includes a sensor for sensing the skin temperature of at least one finger of a human subject.

12. The system of claim 9 including an earphone adapted to be worn by the subject during said predetermined time interval to block out ambient noise or to receive white noise to reduce or eliminate audio stimulus from the ambient environment during said time interval.

13. The system of claim 12 including a source of white noise coupled to said earphone to provide white noise during said predetermined time interval.

14. A method of determining whether an individual has Attention Deficit Disorder (ADD) comprising:
sampling a physiological parameter of a human subject during a predetermined time interval when the subject is in an inactive state to provide sampled physiological parameter data; and
analyzing the sampled physiological parameter data for a pre-selected parameter, to determine whether said pre-selected parameter has a value indicative of ADD.

\* \* \* \* \*